United States Patent [19]

Patel

[11] Patent Number: 4,867,984

[45] Date of Patent: Sep. 19, 1989

[54] DRUG IN BEAD FORM AND PROCESS FOR PREPARING SAME

[75] Inventor: Nagin K. Patel, 1914 W. 5th St., Brooklyn, N.Y. 11223

[73] Assignee: Nagin K. Patel, Matawan, N.J.

[21] Appl. No.: 312,410

[22] Filed: Feb. 17, 1989

Related U.S. Application Data

[63] Continuation of Ser. No. 161,215, Feb. 17, 1988, abandoned, which is a continuation of Ser. No. 668,923, Nov. 6, 1984, abandoned.

[51] Int. Cl.$^4$ .................. A61K 9/16; A61K 9/32; A61K 9/52; A61K 31/79
[52] U.S. Cl. .................. 424/458; 424/462; 424/482; 424/489; 424/490; 424/497; 424/80
[58] Field of Search ............ 424/80, 458, 462, 482, 424/489, 490, 497

[56] References Cited

U.S. PATENT DOCUMENTS

| | | | |
|---|---|---|---|
| 2,811,483 | 10/1957 | Aterno et al. | 424/35 |
| 2,853,420 | 9/1958 | Lowey | 424/35 |
| 2,928,770 | 3/1960 | Bardani | 424/35 |
| 3,155,590 | 11/1964 | Miller et al. | 167/83 |
| 3,341,416 | 9/1967 | Anderson et al. | 167/83 |
| 3,344,029 | 9/1967 | Berger | 424/35 |
| 3,400,185 | 9/1968 | Kohnle et al. | 424/35 |
| 3,415,758 | 12/1968 | Powell et al. | 252/316 |
| 3,420,931 | 1/1969 | Daum et al. | 424/35 |
| 3,446,891 | 5/1969 | Cavalli et al. | 424/35 |
| 3,488,418 | 1/1970 | Holliday et al. | 424/35 |
| 3,492,397 | 1/1970 | Peters et al. | 424/35 |
| 3,524,910 | 8/1970 | Holliday et al. | 424/35 |
| 3,835,221 | 9/1974 | Fulberth et al. | 424/35 |
| 3,851,032 | 11/1974 | Andrews et al. | 424/80 |
| 3,882,228 | 5/1975 | Boncey et al. | 424/35 |
| 3,906,086 | 9/1975 | Guy et al. | 424/20 |
| 3,917,813 | 11/1975 | Pedersen | 424/35 |
| 4,083,949 | 4/1978 | Benedickt | 424/35 |
| 4,138,475 | 2/1979 | McAinsh et al. | 424/21 |
| 4,173,626 | 11/1979 | Dempski et al. | 424/37 |
| 4,268,496 | 5/1981 | Shigeru et al. | 424/19 |
| 4,308,251 | 12/1981 | Dunn et al. | 424/19 |
| 4,339,428 | 7/1982 | Tencza | 424/21 |
| 4,344,934 | 8/1982 | Martin et al. | 424/80 |
| 4,367,217 | 1/1983 | Gruber et al. | 424/35 |
| 4,375,468 | 3/1983 | Dunn | 424/230 |
| 4,412,986 | 11/1983 | Kawata et al. | 424/80 |
| 4,415,547 | 11/1983 | Yu et al. | 424/19 |
| 4,427,648 | 1/1984 | Brickl et al. | 424/35 |
| 4,438,091 | 3/1984 | Gruber | 424/21 |
| 4,443,497 | 4/1984 | Samejima et al. | 427/213.36 |
| 4,555,399 | 11/1985 | Hsiao | 424/80 |
| 4,562,024 | 12/1985 | Rogerson | 514/629 |
| 4,562,061 | 12/1985 | Appelgren et al. | 424/35 |
| 4,562,069 | 12/1985 | Hegasy et al. | 424/80 |

FOREIGN PATENT DOCUMENTS

| | | |
|---|---|---|
| 742007 | 12/1955 | United Kingdom . |
| 844772 | 8/1960 | United Kingdom . |
| 1326995 | 8/1973 | United Kingdom . |
| 1561301 | 2/1980 | United Kingdom . |

OTHER PUBLICATIONS

Junginger GA., 85#130430f (1976).
Junginger Ga., 88#158383D (1978).
Erbeia Ga., 91#163052m (1979).
Andrews Ga., 82#64542d (1975).
Lipman Ga., 94#127245e (1981).
Eide Ga., 79#57618T (1973).
Hurn Ga., 97#168795Q (1982).
Higuchi, Horn, Merkle, Ga., 102#32107F, #32108q, #32109H (1985), 1983, Proc. Int. Symp. Povidone 71–100, 202–216.
"Formulation and Manufacture of the Sustained Action Dosage Form", J. Lachman, *The Theory and Practice of Industrial Pharmacy*, 2nd Edition, 1976, pp. 456–459.

*Primary Examiner*—Shep K. Rose
*Attorney, Agent, or Firm*—Blum Kaplan

[57] ABSTRACT

A bead of a drug such as aspirin or acetaminophen formed from a small spheriodal seed particle of the drug or of an inert material coated with an adhesive and layers of drug particles likewise adhered by said adhesive, is provided. The beads may be rendered suitable for time release by coating a plurality of said beads. An 8–12% polyvinylpyrrolidone (PVP) solution may be used as the adhesive, the PVP complexing with aspirin and acetaminophen to reduce irritation of the user. Additionally, a method for manufacturing a drug in small beads having time releasae properties is also provided.

37 Claims, No Drawings

DRUG IN BEAD FORM AND PROCESS FOR PREPARING SAME

This is a continuation of application Ser. No. 07/161,215, filed Feb. 17, 1988, now abandoned which is a continuation of application Ser. No. 06/668,923 filed Nov. 6, 1984, now abandoned.

BACKGROUND OF THE INVENTION

This invention relates to a method for manufacturing a drug, especially aspirin, acetaminophen, or the like, in small beads to be placed in a capsule and to the drug thus produced. In particular, the method involves preparation of a drug using a coating, such as an aqueous polymeric coating, on at least a portion of the beads, which results in sustained release when traveling through the digestive system.

Time release capsules containing a drug are made by either microencapsulation or by coating a seed, referred to as the Nupareil seed coating process. In both the encapsulation process and the Nupareil seed coating process, however, it is not feasible to obtain 650 mg of the active ingredient in bead form to be enclosed in a zero sized capsule. In a microencapsulation process, nearly 25% of the capsule is sugar, starch and moisture with the remainder being the active ingredient. Consequently, only 450-500 mg of active ingredient may be contained in a zero sized capsule. In the Nupareil seed coating process, seeds are relatively large, commonly 20-40 mesh and, thus, coated seeds do not permit more than 500-550 mg to be encapsulated in bead form in a zero sized capsule.

An additional process involves granulation, in which the drug used is combined with a starch and other materials, including an adhesive, and the material is then forced through a screen. This process, however, also limits the amount of drug that can be encapsulated to less than 550 mg.

In U.S. Pat. No. 3,524,910 to Holiday et al., granules of aspirin are encapsulated in a gelatin capsule. Additionally, the patent discloses sustained release of a portion of the active ingredient over an extended period of time by coating some of the granules with ethylcellulose in order to provide an analgesic effect of prolonged duration. However, the Holiday et al. delayed release aspirin compound capsule has disadvantages in that a zero sized capsule would not be sufficiently large in volume for holding the aspirin compound. Additionally, ingestion of the aspirin compound may produce undesired gastric irritation.

Accordingly, it is desirable to provide an improved method for manufacturing sustained release aspirin in a capsule.

SUMMARY OF THE INVENTION

Generally speaking, in accordance with the present invention, a bead of a drug is provided formed from a small spheroidal seed particle of the drug coated with an adhesive and layers of particles of the drug likewise adhered by said adhesive. The bead may be rendered suitable for time release by a suitable coating and a plurality of said beads, both coated and uncoated, may be provided in a capsule for dosage control. The drug is preferably aspirin, acetaminophen, or the like. The adhesive is preferably polyvinylpyrrolidone (PVP). In the case where the drug is aspirin or acetaminophen, the adhesive is selected to complex with the aspirin or acetaminophen. The core is preferably essentially spheroidal and of 60-80 mesh size. In the case of aspirin, acetaminophen or like product, the core may be an essentially spheroidal seed particle formed from a pharmacologically suitable material such as potassium chloride or microcrystalline cellulose. The resultant drug beads consist of at least 50% by weight of the drug and preferably in excess of 90% by weight.

Further, in accordance with the present invention, a method for manufacturing a drug in small beads to be placed in a capsule is provided, preferably in a time release form. In accordance with the method, small, essentially spheroidal seed particles of a pharmacologically suitable material such as potassium chloride or microcrystalline cellulose, are coated by aspirin, acetaminophen, or other drug particles by placing the particles in a rotating coating pan containing baffles. Alternatively, small essentially spheroidal cores of active drug ingredient are coated by placing them in a rotating coating pan containing baffles. The baffles rotate the particles for a uniform coating.

A solution of a suitable adhesive, preferably a solution of polyvinylpyrrolidone (PVP) in isopropyl alcohol, is added to the coating pan in order to wet the particles' surfaces. Following the addition of the adhesive, a small amount of the active ingredient in particulate form is entered into the coating pan and adheres to the coated spheroidal particles. The particles are then dried and the process is repeated until small beads are formed, comprising approximately 50-98% of active ingredient.

Afterwards, a portion of the beads may be coated with an aqueous polymeric coating in order to prevent immediate dissolution in the digestive tract. All the beads are then placed in a capsule, such as a zero or A sized capsule, for later medicinal use.

If the active ingredient is aspirin, it is found that a PVP-aspirin complex is formed which reduces gastic irritation. Similar complexing is found in the case of acetaminophen.

Accordingly, it is an object of the invention to provide an improved method of manufacturing a drug.

Yet another object of the invention is to provide an improved method of manufacturing a drug in small beads to be placed in a capsule.

It is still a further object of the invention to provide an improved method for manufacturing a drug for enclosure of 650 mg in a zero or A sized capsule.

Still another object of the invention is to provide an improved method for manufacturing a drug for effective time release.

It is a further object of the invention to produce a bead form of drug suitable for time release coating and consisting of at least 50% by weight and preferably in excess of 90% by weight of the drug.

It is still another object of the invention to produce a bead form of aspirin, acetaminophen or the like.

Still other objects and advantages of the invention will, in part be obvious and will in part be apparent from the specification.

The invention accordingly comprises the several steps and the relation of one or more of such steps with respect to each of the others, and the composition possessing the features, properties, and the relation of components, which are exemplified in the following detailed disclosure, and the scope of the invention will be indicated in the claims.

DESCRIPTION OF THE PREFERRED EMBODIMENTS

In a first embodiment of the invention, essentially spheroidal core particles of active ingredient ranging from 60 to 80 mesh are placed in a conventional coating pan having a baffle system attached thereto. The coating pan rotates about an axis defining an acute angle with the horizontal plane, with particles tending to remain at the lower region thereof. The inwardly projecting, V-shaped baffles help the particles rotate during the coating operation. The baffle system extends essentially parallel to the axis of rotation of the coating pan, the walls of the baffles defining a 0°-45° angle with respect to said axis of rotation, and preferably a 15° angle.

A solution of polyvinylpyrrolidone (PVP) in isopropyl alcohol is added to the coating pan and poured over the core material to sufficiently wet each particle's surface. The PVP solution serves as an adhesive and may range from 8 to 12%, but preferbaly is a 10% solution. The amount of PVP solution is selected to be sufficient to wet the surface of the drug particles. An excess of PVP should be avoided to aid in avoiding agglomeration. Optionally, a small amount of talc or other suitable lubricant, such as magnesium stearate, is added to minimize particle agglomeration. Manual or mechanical agitation may also aid in preventing the beads from sticking to each other.

Following the addition of PVP adhesive, the active ingredient in powder form, 60-80 mesh, is sprinkled into the coating pan, thereby sticking to the coated spheroidal cores. This process is then repeated from four to eight times, preferably five times, with the addition of PVP solution at each repetition.

The particles are then dried by means of a warm-air blower, until completely dried. The particular drying mechanism should provide fast drying and thus, a warm-air flow between the temperature ranges of 40° C. to 60° C. is preferable.

After drying, the process of adding active ingredient and PVP adhesive is repeated between 10-50 times, preferably 30-40 times. It is to be noted that no more talc is added at this particular stage. Once the process of adding the active ingredient and PVP solution is completed, the rotating coating pan will contain essentially spheroidal beads comprising approximately 50%-98% active ingredient, preferably 90%-95%. These beads are dried on a tray for a period of 6-8 hours, in order to remove traces of isopropyl alcohol. The tray dryer should be at a temperature between 40°-45° C.

The next step consists of coating 25-75%, preferably 50%, of the beads with an aqueous polymeric solution. The aqueous polymer is preferbaly ethylcellulose "pseudolatex" (sold under the trademark AQUACOAT) having a solution concentration between about 3.5%-20.0%, but may also be an anionic polymer synthesized from a methacrylic acid and methacrylic acid methylester (sold under the trademark EUDRAGIT L). The coating is applied in order to prevent immediate dissolution in the stomach so that the product has time release properties.

In accordance with the invention, the aqueous polymeric solution is coated on the beads by use of an air-suspension coating device, such as an Aeromatic Strea-1, made by the Aeromatic Company. In this process, beads are suspended in a column which is supplied with warm, compressed air while the solution is sprayed into the column. The liquid spray is coated on the beads and immediately dried in warm air. Due to evaporation, surface temperature drops, thus minimizing the decomposition of aspirin. After the first coat is dry, water can no longer attack the aspirin. All the beads are then put into a zero sized or A sized capsule for packaging in a medicinal container.

In a further embodiment of the invention, coating of various pH sensitive acrylic polymers may be placed on the beads not coated with an aqueous acrylic polymer. Roughly one-half of the uncoated beads are coated with a polymer which is pH 6 sensitive while the other one-half are coated with a polymer which is pH 7 sensitive. These various coatings promote dissolution along various points in the alimentary canal.

In an alternative method the drug is manufactured by first using small, spheroidal seed particles, ranging from 60 to 80 mesh such as potassium chloride or microcrystalline cellulose. These particles are placed in a rotating coating pan having a baffle system attached thereto. A solution of PVP in isopropyl alcohol is added to the coating pan to serve as an adhesive. Optionally, talc may be added. Following the addition of the PVP adhesive, powdered active ingredient, 60-80 mesh, is sprinkled into the coating pan, thereby sticking to the coated seed particle. The process continues in the same manner as discussed previously.

Depending on the active ingredient used in the starter core or the composition used in the seed particle, it may be necessary to first round off the core or seed before placement in the coating pan. Such is the case when potassium chloride is used as seed particles or aspirin is used for starter core particles. Consequently, 60-80 mesh seed or core particles are first placed in a Hobart mixer. By simultaneously mixing the particles and adding a small amount of alcohol or hydroalcoholic solution, the individual particles are rounded-off and become spheroidal in shape.

In the specific case where aspirin or acetaminophen is the active ingredient, the aspirin or acetaminophen forms a molecular complex with the polyvinylpyrrolidone. In testing, it was found that the aspirin product in accordance with the invention was characterized by reduced gastric irritation. Similarly, it is expected that the acetaminophen product would be characterized by reduced gastric irritation. This is due to a layered complex in the product since each PVP coated layer dissolves aspirin or acetaminophen in successive stages within the stomach. These complexes are similar to a PVP-iodine complex which eliminates irritation of iodine when a PVP-iodine product is placed on abraded skin. These complexes are shown to be present by the conventional equilibrium dialysis technique.

The following examples are intended to illustrate the invention and should not be construed as limiting the invention thereto.

EXAMPLE 1

100 grams of microcrystalline cellulose particles, 60 to 80 mesh, were placed into a 16 inch pear-shaped conventional coating pan. The pan had a triangular baffle system attached at a 15° angle to the axis of rotation to the pan. After the pan was turned on, 10% polyvinylpyrrolidone solution in isopropyl alcohol was poured over the microcrystalline cellulose particles in order to wet the particles' surfaces. Aspirin powder, 60 to 80 mesh, was then sprinkled into the pan. A small amount of talc was also added to prevent particle agglomeration. The steps of adding PVP solution, sprinkling aspirin powder and adding talc were repeated five times. The resulting particles were then dried by means of a warm air blower at a temperature of about 50° C. After drying, the steps of sprinkling aspirin powder and adding PVP solution were repeated 40 times until small beads were formed comprising 90 to 95% aspirin. The beads were then separated into equal parts. One part was coated with a 5% ethylcellulose "pseudolatex" solution (sold under the trademark AQUACOAT) which included 1% dibutylphthalate as plasticizer and purified water as solvent. The solution was coated on the beads by use of an air suspension coating device wherein the beads were suspended in a column supplied with warm, compressed air onto which the solution was sprayed. After coating the beads, the beads were immediately dried in warm air. Following coating, each bead had a weight gain of 1.5% ethylcellulose "pseudolatex" and 1% dibutylphthalate. Two equal parts of coated and uncoated beads having a diameter ranging from about 1.8-3.0 mm were then mixed in order to get a weight equivalent of 650mg of aspirin. The beads were placed into an A sized (sold under the trademark CONI SNAP SUPRO) gelatin capsule.

EXAMPLE 2

Using the product of Example 1 in comparison with that of Bayer's time released aspirin, dissolution of the drugs using the United States Pharmacopia test was compared. After choosing five healthy volunteers, a randomized crossover design study was performed to compare the "in vivo" release of each analgesic. Each subject ingested the product of Example 1 and Bayer's time released tablet. Both contained 650 mg of aspirin. The amount of analgesic excreted in the urine was then measured at various time intervals. The results showed that the encapsulated aspirin of Example 1 compared well with Bayer's commercial product with regard to release pattern. Additionally, the subjects reported substantially lesser irritation when using the composition in accordance with the invention.

EXAMPLE 3

300 grams of potassium chloride, 60 to 80 mesh, were placed in a Hobart mixing bowl having a 2 liter capacity. The mixer was set at speed of 450 rpm and then turned on. A small amount of 70% ethyl alcohol in water was added to the bowl in order to help round off the potassium chloride crystals. After 5 minutes of mixing, the potassium chloride particles were air dried on a tray. 100 grams of potassium chloride particles were then placed into a 16 inch pearshaped conventional coating pan. The pan had a triangular baffle system attached at a 15° angle of rotation to the pan. After the pan was turned on, 10% PVP solution in isopropyl alcohol was poured over the potassium chloride particles in order to wet their surfaces. Aspirin powder, 60 to 80 mesh, was then sprinkled into the pan. A small amount of talc was also added to prevent particle agglomeration. The steps of adding PVP solution, sprinkling aspirin and adding talc were repeated five times. After drying, the steps of sprinkling aspirin powder and adding PVP solution were repeated 40 times, as in Example 1, until small beads were formed comprising approximately 90 to 95% aspirin. The beads were then separated into three groups of 50%, 25% and 25% by weight. The 50% group was left unchanged. The second group (25%) was coated with an aqueous anionic polymer solution synthesized from methacrylic acid and methacrylic acid methylester (sold under the trademark EUDRAGIT L). The beads were coated using the air suspension coating method of Example 1. Following coating, each bead had a weight gain of 15% anionic polymer. The third group (25%) was coated with a 20% alcoholic anionic polymer solution in a similar manner as the second group except that the anionic polymer was dissolved in isopropyl alcohol rather than water. The solution also contained 15% dibutylphthalate as plasticizer. Each bead of the third group had a weight gain of 15% anionic polymer and 15% dibutylphthalate. Thereafter, the three groups of beads having a diameter ranging from about 1.8-3.0 mm were mixed in order to get a weight equivalent of 650mg of aspirin. The beads were placed in an A sized gelatin capsule.

EXAMPLE 4

300 grams of aspirin, 60 to 80 mesh, were placed in a Hobart mixing bowl having a 2 liter capacity. The mixer was set at speed of 450 rpm and then turned on. A small amount of pure isopropyl alcohol was added in order to help round off the aspirin particles. After 5 minutes of mixing, the particles were air dried on a tray. 100 grams of aspirin particles were then placed into a 16 inch coating pan. The pan had a triangular baffle system. The baffle system was placed at a 15° angle of rotation to the pan. After turning on the pan, 10% PVP solution in isopropyl alcohol was poured over the aspirin particles in order to wet their surfaces. Aspirin powder, 60 to 80 mesh, was then sprinkled into the pan. A small amount of talc was also added to prevent particle agglomeration. The process was then continued as in Example 1. A weight equivalent of 650 mg of aspirin in bead form were placed in a zero sized gelatin capsule.

EXAMPLE 5

300 grams of spheroidal particles containing acetaminophen and chlorpheniramine maleate in the ratio of 325 to 2 by weight (sold under the trademark COMPAP-CPM), were placed into a 16 inch coating pan. The pan had a triangular baffle system attached at a 15° angle to the axis of rotation to the pan. After the pan was turned on, 10% PVP solution in isopropyl alcohol was poured over the particles in order to wet the particles' surfaces. Acetaminophen powder, 60 to 80 mesh, was then sprinkled into the pan. A small amount of talc was also added to prevent particle agglomeration. The steps of adding PVP solution, sprinkling acetaminophen and adding talc were repeated five times. The resulting particles were then dried by means of a warm air blower at a temperature of approximately 50° C. The steps of sprinkling acetaminophen powder and adding PVP solution were repeated 35 times until small beads were formed, comprising 90 to 95% acetaminophen. The beads were then coated with an aqueous polymeric solution in accordance with the procedure set forth in Example 1 in order to get a weight equivalent of 650 mg of acetaminophen in beads. The beads were placed in a zero sized gelatin capsule.

EXAMPLE 6

The method of Example 1 was followed except that 3.5% ethyl cellulose "pseudolatex" solution (sold under the trademark AQUACOAT) including 1% dibutylphthalate as plasticizer was used to coat the beads. Following coating, each bead had a weight gain of 1.0% ethylcellulose "pseudolatex" and 10% dibutylphthalate. Two equal parts of coated and uncoated beads ranging from about 1.8–3.0 mm were then mixed to get a weight equivalent of 650 mg of aspirin. The beads were placed into an A sized gelatin capsule.

EXAMPLE 7

The method of Example 1 was followed except that 20.0% ethylcellulose "pseudolatex" including 1% dibutylphthalate as plasticizer was used to coat the beads. Following coating, each bead had a weight gain of 6.0% ethyl cellulose "pseudolatex" and 1% dibutylphthalate. Two equal parts of coated and uncoated beads ranging from about 1.8–3.0 mm were then mixed to get a weight equivalent of 650 mg of aspirin. The beads were placed in a zero sized gelatin capsule.

EXAMPLE 8

The method of Example 1 was followed except that 8.0% PVP solution in isopropyl alcohol was used as adhesive. Small beads were formed comprising 90–95% aspirin which were then coated with an aqueous polymeric coating as Example 1 states. Two equal parts of coated and uncoated beads ranging from about 1.8–3.0 mm were then mixed to get a weight equivalent of 650 mg of aspirin. The beads were placed in a zero sized gelatin capsule.

EXAMPLE

The method of Example 1 was used except that 12.0% PVP solution in isopropyl alcohol was used as an adhesive. Small beads were formed comprising 90–95% aspirin which were then coated with an aqueous polymeric coating as Example 1 states. Two equal parts of coated and uncoated beads ranging from about 1.8–3.0 mm were then mixed to get a weight equivalent of 650 mg of aspirin. The beads were placed in an A sized gelatin capsule.

The final aspirin products in Examples 1–4 and 6–9 were tested for free salicylic acid content according to U.S. pharmacopia procedure. The aspirin products were found to be within U.S. Pharmacopia specification.

Although polyvinylpyrrolidone (PVP) in isopropyl alcohol is the adhesive composition disclosed in the examples, any suitable adhesive material which is non-toxic and non-allergenic, preferably a natural or synthetic polymer, and preferably a complexing agent, may be used for coating the seed particles and adhering layers of drug particles.

Additionally, although aqueous and alcohol-based polymeric coatings are the coatings for preventing immediate dissolution of the drug in the digestive tract disclosed in the examples, it is understood that any suitable coating which results in sustained release when travelling through the digestive tract may be used.

While microcrystalline cellulose and potassium chloride particles are used as seeds in the examples, any suitable pharmacologically inert material capable of formation with small sized spheroidal material may be used as seeds in addition to particles of the drug itself.

Although a conventional coating pan having a baffle system attached thereto is used in the examples, commercial high-speed rotation granulators may also be used for formation of beads from spheroidal seed particles.

Furthermore, although aspirin and acetaminophen are the drugs disclosed in the examples the method of manufacture of bead forms of drugs in accordance with the invention is suitable for any drug available in powered form.

It will thus be seen that the objects set forth, among those made apparent from the preceding description, are efficiently obtained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following claims are intended to cover all the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

What is claimed is:

1. An aspirin product comprising a plurality of beads not compressed into a tablet, each bead being formed of a central, small, essentially spheroidal seed and successive layers formed from powdered aspirin substantially complexed with the polyvinylpyrrolidone in an adhesive comprising from about an 8 to about a 12% solution of polyvinylpyrrolidone in alcohol, each successive layer of the substantially complexed aspirin and polyvinylpyrrolidone being adhered to the seed or to the preceeding layer by the adhesive, the bead including at least 50% by weight of aspirin, whereby the aspirin product reduces gastric irritation.

2. The aspirin product of claim 1, wherein the seed is formed of pharmacologically inert material formed into an essentially spheroidal particle.

3. The aspirin product of claim 2, wherein the seed material is selected from the group including potassium chloride and microcrystalline cellulose.

4. The aspirin product of claim 1, wherein the seed is formed of aspirin.

5. The aspirin product as recited in claim 1, wherein the bead is coated with a suitable time release material.

6. The aspirin product as recited in claim 5, wherein the time release material includes a material selected from the group including ethylcellulose "pseudolatex", an aqueous anionic polymer and an alcoholic anionic polymer.

7. The aspirin product as recited in claims 1, wherein the bead includes at least 90% by weight of aspirin.

8. The aspirin product as recited in claims 1, and including a plurality of said beads encapsulated in a capsule.

9. The aspirin product as recited in claim 8, wherein the capsule is selected from the group including zero and A sized capsules.

10. The aspirin product as recited in claim 9, wherein at least a portion of the beads are coated with a suitable time release material.

11. An acetaminophen product comprising a plurality of beads not compressed into a tablet, each bead being formed of a central, small, essentially spheroidal seed and successive layers formed from powdered acetaminophen substantially complexed with the polyvinylpyrrolidone in an adhesive comprising from about an 8 to about 12% solution of polyvinylpyrrolidone in alcohol, each successive layer of the substantially complexed acetaminophen and polyvinylpyrrolidone being adhered to the seed or to the preceding layer by the adhesive, the bead including at least 50% by weight of acetaminophen.

12. The acetaminophen product as recited in claims 11 or 19 wherein the seed is 60-80 mesh in size.

13. The acetaminophen product of claim 12, wherein the seed is formed of pharmacologically inert material formed into an essentially spheroidal particle.

14. The acetaminophen product of claim 13, wherein the seed material is selected from the group including potassium chloride and microcrystalline cellulose.

15. The acetaminophen product of claim 11, wherein the seed is formed of acetaminophen.

16. The acetaminophen product of claim 15, wherein the seed of acetaminophen is 60-80 mesh in size.

17. The acetaminophen product as recited in claims 11 or wherein the bead is coated with a suitable time release material.

18. The acetaminophen product as recited in claim 17, wherein the time release material includes a material selected from the group including ethylcellulose "pseudolatex", an aqueous anionic polymer and an alcoholic anionic polymer.

19. The acetaminophen product as recited in claims 11 wherein the bead includes at least 90% by weight of acetaminophen.

20. The acetaminophen product as recited in claims 11, and including a plurality of said beads encapsulated in a capsule.

21. The acetaminophen product as recited in claim 20, wherein the capsule is selected from the group including zero and A sized capsules.

22. The acetaminophen product as recited in claim 21, wherein at least a portion of the beads are coated with a suitable time release material.

23. A drug product comprising a plurality of beads not compressed into a tablet, each bead being formed of a small, essentially spheroidal central seed of a drug material selected from the group consisting of aspirin, acetaminophen and mixtures thereof and successive layers of small particles of said drug material substantially complexed with the polyvinylpyrrolidone in an adhesive comprising about an 8 to about 12% solution of polyvinylpyrrolidone in alcohol, each successive layer of the substantially complexed drug material and polyvinylpyrrolidone being adhered to the seed or the preceding layer by the adhesive.

24. A drug product as recited in claim 23, wherein the bead includes at least 50% of weight of the drug.

25. A drug product as recited in claim 24, wherein the bead includes at least 90% by weight of the drug.

26. A drug product as recited in claim 23, and including a plurality of said beads, at least a portion of said beads including a time release coating.

27. The aspirin product of claim 1, wherein the seed is 60-80 mesh in size.

28. The aspirin product of claim 1, wherein the powdered aspirin has a mesh size of about 60 or more.

29. The aspirin product of claim 28, wherein the central seed and powdered aspirin has a mesh size of from about 60 to about 80, the seed is selected from the group including aspirin, potassium chloride and micro-crystalline cellulose, and including a gelatin capsule containing said plurality of beads.

30. The aspirin product of claim 29, wherein at least a portion of the beads are coated with a suitable time-release material.

31. The acetaminophen product of claim 11, wherein the powdered acetaminophen has a mesh size of about 60 or more.

32. The acetaminophen product of claim 31, wherein the central seed and powdered acetaminophen has a mesh size of from about 60 to about 80, the seed is selected from the group including acetaminophen, potassium chloride and micro-crystalline cellulose, and including a gelatin capsule containing said plurality of beads.

33. The acetaminophen product of claim 32, wherein at least a portion of the beads are coated with a suitable time-release material.

34. The drug product of claim 23, wherein the drug product particles have a mesh size of about 60 or more.

35. The drug product of claim 34, wherein the seeds and the granules of said drug material are about 60-80 mesh in size, and including a gelatin capsule carrying said plurality of beads.

36. The drug product of claim 35, wherein at least a portion of said beads are coated with a suitable time-release material.

37. The drug product of claim 23, wherein the essentially central spheroidal see is about 60-80 mesh in size.

* * * * *